United States Patent
Jeong et al.

(10) Patent No.: US 8,018,582 B2
(45) Date of Patent: Sep. 13, 2011

(54) SIMULTANEOUS DETECTION APPARATUS OF RAMAN AND LIGHT SCATTERING

(75) Inventors: Dae-Hong Jeong, Gwanak-gu (KR);
Yoon-Sik Lee, Anyang-si (KR);
Myung-Haing Cho, Seocho-gu (KR);
Yong-Kweon Kim, Gangnam-gu (KR)

(73) Assignee: SNU R&DB Foundation, Seoul (KR)

( * ) Notice: Subject to any disclaimer, the term of this patent is extended or adjusted under 35 U.S.C. 154(b) by 176 days.

(21) Appl. No.: 12/442,109

(22) PCT Filed: Aug. 30, 2007

(86) PCT No.: PCT/KR2007/004183
§ 371 (c)(1),
(2), (4) Date: Apr. 13, 2009

(87) PCT Pub. No.: WO2008/035864
PCT Pub. Date: Mar. 27, 2008

(65) Prior Publication Data
US 2010/0020312 A1    Jan. 28, 2010

(30) Foreign Application Priority Data
Sep. 19, 2006    (KR) .................. 10-2006-0090516

(51) Int. Cl.
*G01J 3/44*    (2006.01)
*G01N 21/47*    (2006.01)
*G01N 21/64*    (2006.01)
*G01N 21/65*    (2006.01)

(52) U.S. Cl. .......... 356/73; 356/301; 356/317; 356/339; 356/342

(58) Field of Classification Search .............. 356/73, 356/301
See application file for complete search history.

(56) References Cited

U.S. PATENT DOCUMENTS

| 3,850,525 | A | * | 11/1974 | Kaye ................. 356/73 |
| 4,071,298 | A | * | 1/1978 | Falconer ............ 356/73 |
| 5,870,188 | A | | 2/1999 | Ozaki et al. |
| 6,256,097 | B1 | | 7/2001 | Wagner |
| 2002/0039184 | A1 | | 4/2002 | Sandusky |

FOREIGN PATENT DOCUMENTS

| JP | 09145619 | 6/1997 |
| JP | 09243569 | 9/1997 |
| KR | 10-1999-0080483 | 11/1999 |
| KR | 10-2003-0041147 | 5/2003 |
| WO | WO 03/042646 | 5/2003 |

\* cited by examiner

*Primary Examiner* — Fannie L. Evans
(74) *Attorney, Agent, or Firm* — Sherr & Vaughn, PLLC

(57) ABSTRACT

Provided is a detection apparatus of Raman scattering and light scattering, and more particularly, a simultaneous detection apparatus of Raman scattering and dynamic light scattering and a detection method using the same. The simultaneous detection apparatus of Raman scattering and light scattering includes: a detection unit for applying incident light to a sample, and detecting Raman scattering in 90° or 180° geometry and light scattering in 90° or 180° geometry in order to simultaneously collect Raman scattering and light scattering; and a computer connected to the detection unit to obtain at least one of the size and distribution of particles from the detected light scattering, and to obtain information of the molecular structure from the detected Raman scattering. This apparatus may simultaneously observe the size of nano-sized or larger material and molecular information thereof, and phenomena accompanying changes in molecular environment according to material variation and changes of the material in size and distribution, and thus is very useful for studying nano materials and protein antigens and antibodies.

12 Claims, 4 Drawing Sheets

SIMULTANEOUS DETECTION APPARATUS OF RAMAN AND LIGHT SCATTERING

The present application is a National Stage application of PCT International Patent Application No. PCT/KR2007/004183 (filed on Aug. 30, 2007) which claims priority to Korean Patent Application No. 10-2006-0090516 (filed on Sep. 19, 2006) which are hereby incorporated by reference in its entirety.

TECHNICAL FIELD

The present invention relates to an apparatus capable of detecting Raman and light scattering, and more particularly, to an apparatus capable of simultaneously detecting Raman and light scattering and a detection method using the same.

BACKGROUND ART

Detection apparatuses of Raman and light scattering detect information of a molecule's vibrational structure and particle's size and distribution, respectively. The Raman scattering causes a change in vibration potential of a molecule, and vibration frequency and structural information of the molecule are obtained by measuring the frequency shift of the scattered light from the incident light. Such Raman scattering is inelastic, and scattering energy intensity is approximately $\frac{1}{1000}$ of that of elastic scattering. Thus, in the Raman scattering, a light collection device needs a device for removing elastic scattered light.

Meanwhile, the light scattering detection apparatus detects size and distribution of nano-sized particles, wherein the light scattering corresponds to elastic scattering. The energy intensity of the light scattering is determined by angle formed between the incident light and scattered light, and thus light scattering collection angle has to be small as much as possible, and inelastic light, which is relatively weak, does not need to be removed.

According to known arts so far, while the Raman scattering and light scattering have been individually detected by common apparatuses which had been developed separately, any simultaneous detection result of the Raman scattering and light scattering has not been reported. Thus, when an environment of molecules constituting an object material are changed according to changes of the object material in size and shape, the changes of the molecular environment, and its size and shape can not be simultaneously detected. Particularly, phenomena such as growth and change of a nano material, binding between a nanomaterial and protein, and reaction between an antigen and an antibody may often go with the changes of the material's size and its molecular environment. The prior arts have problems in that, in order to study such phenomena, both detection apparatuses for Raman scattering and light scattering should be equipped at the same time, and light sources thereof are difficult to be altered, if necessary. That is, the prior arts have difficulty in simultaneously analyzing information such as chemical characteristics of components according to the kinds of samples, environmental changes, sizes and shapes of the components around the sample.

DISCLOSURE

Technical Problem

The present invention is directed to an apparatus which is capable of simultaneously detecting Raman and light scattering from the same volume of sample illuminated by an incident light.

Technical Solution

One aspect of the present invention provides a simultaneous detection apparatus of Raman and light scattering, comprising: a detection means for applying incident light to a sample, and detecting Raman scattering in 180° geometry and light scattering in 90° geometry in order to simultaneously collect the Raman scattering and the light scattering; and a computer connected to the detection means to obtain at least one of the size and distribution of particles from the detected light scattering, and to obtain information on the molecular structure from the detected Raman scattering.

Another aspect of the present invention provides a simultaneous detection apparatus of Raman and light scattering; which includes: a detection means for applying incident light to a sample, and detecting Raman scattering in 90° geometry and light scattering in 90° geometry; and a computer connected to the detection means to obtain at least one of the size and distribution of particles from the detected light scattering, and to obtain information of the molecular structure from the detected Raman scattering.

Still another aspect of the present invention provides a simultaneous detection apparatus of Raman and light scattering, which includes: a detection means for applying incident light to a sample, and detecting Raman scattering in 180° geometry and light scattering in 180° geometry in order to simultaneously collect the Raman scattering and the light scattering; and a computer connected to the detection means to obtain at least one of the size and distribution of particles from the detected light scattering and to obtain information of the molecular structure from the detected Raman scattering.

Advantageous Effects

As described above, the present invention may simultaneously detect Raman and light scattering with respect to one sample, thereby analyzing information on size of a nano-sized material and molecules constituting the material. That is, the present invention is a means for observing changes in size and molecular environment of the material in terms of phenomena such as growth and variations of the nano material, binding between the nano material and protein, and reaction between an antigen and an antibody.

MODE FOR INVENTION

Figure 1:
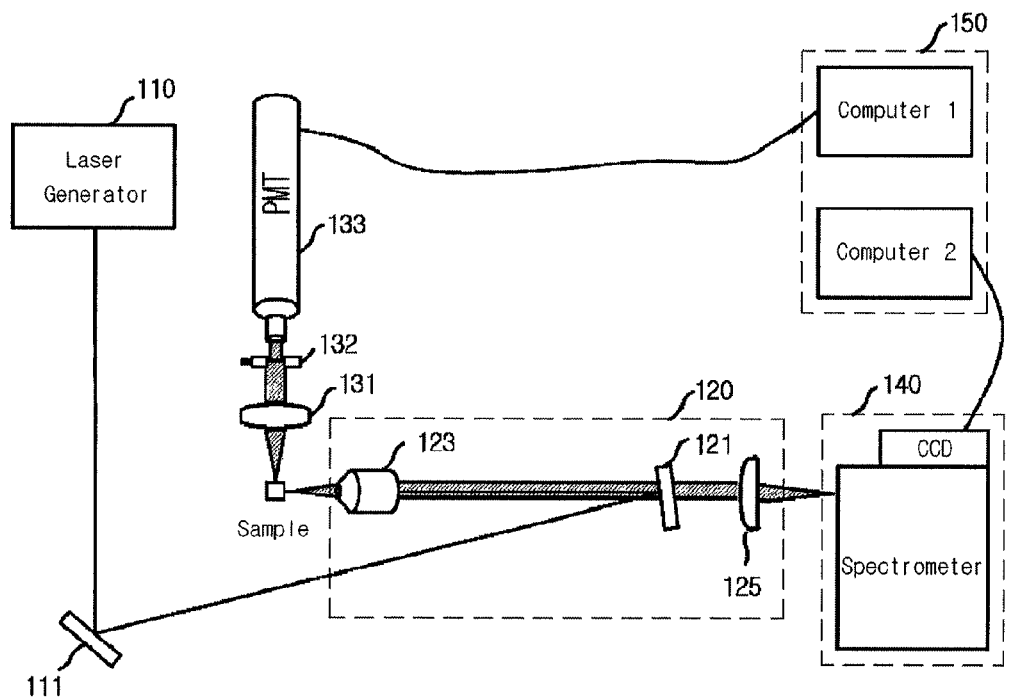
FIG. 1 illustrates a simultaneous detection apparatus of Raman scattering and dynamic light scattering according to an exemplary embodiment of the present invention.

The foregoing objects, features and advantages of the invention will become more apparent from the following more particular description of exemplary embodiments of the invention and the accompanying drawings. In the drawings, like numerals denote like components. Also, when it is determined that detailed descriptions on related technology which are known in the art are unnecessary to fully convey the scope of the invention, descriptions thereof will be omitted. Hereinafter, exemplary embodiments of the present invention will be described in detail.

Recently, among interference filters reflecting light with specific wavelength region and transmitting light with other wavelength region, a notch filter and an edge filter (or a cut-off filter) which have high efficiency and are suitable for Raman scattering detection, have been developed to be used in a Raman scattering detection apparatus. The notch filter reflects light with specific region, and transmits light in other region. Thus, using the notch filter enables elastic scattered light to be perfectly filtered from light which is irradiated to and scattered from a sample, thereby obtaining Raman scattered light. The edge filter also reflects light with shorter wavelength and transmits light with longer wavelength compared to the specific wavelength region, and thus may perfectly filter the elastic scattered light, thereby obtaining the Raman scattered light. Using such characteristics of the notch and edge filters enables the Raman scattered light and the elastic scattered light to be separated from scattered light which is collected by one light collection lens, and Raman scattering and light scattering can be simultaneously detected by separate detection apparatuses, respectively.

In the following Exemplary Embodiments 1 to 3, a light collection device for Raman scattering detection has a 180° geometry, which means that the scattered light collection device is placed at 180° with respect to incident light. The disposition and function of the notch filter are disclosed in U.S. Pat. Nos. 5,442,438 and 5,661,557 and Korean Patent Publication No. 1999-0080483.

Hereinafter, exemplary embodiments of the present invention will be described with reference to the accompanying drawings. However, the embodiments and experimental examples are used and are to be interpreted in a generic and descriptive sense only and not for purposes of limitation.

Exemplary Embodiment 1

Raman Scattering Detection in 180° Geometry and Light Scattering Detection in 90° Geometry Using configurational characteristics of the aforementioned light condensing device enables Raman scattering and dynamic light scattering to be simultaneously detected, as proposed in the present invention. First, the 180° geometry light condensing device, which detects Raman scattered light, removes elastic light from the collected scattered light using a notch filter. The light condensing device for detecting light scattering is disposed in a vertical direction with respect to incident light, and can control a light condensing angle to a small degree, if necessary.

FIG. 1 illustrates a simultaneous detection apparatus of Raman scattering and dynamic light scattering according to Exemplary Embodiment 1 of the present invention.

Referring to FIG. 1, the simultaneous detection apparatus of Raman scattering and light scattering includes a laser generator 110, a Raman scattering detector 120, dynamic light scattering detectors 131 to 133, a spectrometer 140, and a computer 150.

The laser generator 110 generates a laser beam in a visible ray region as an incident light, however the present invention is not limited thereto. The incident laser beam is reflected by a mirror 111, and enter the Raman scattering detector 120.

The Raman scattering detector 120 includes a notch or edge filter 121 as described above, an objective lens 123, and a first light collection lens 125. The incident light which is reflected from the mirror 111 is delivered to the objective lens 123 used to adjust the focus the incidendent light to a sample. When the laser beam is directed to the sample, the incident light is scattered, and some of the light is collected by the objective lens 123 (the 180° detection geometry). Among the scattered light collected by the objective lens 123, elastic light is filtered by the notch filter 121, and Raman scattered light is transmitted to the spectrometer 140 via a light collection lens 125. The spectrometer 140 detects a spectrum of the Raman scattered light using a CCD detector (e.g., Ando, DU401) included in the spectrometer 140. The spectrometer 140 is connected to the computer 150.

The dynamic light scattering detector, like a dynamic light scattering detection means having a conventional configuration, is placed at 90° with respect to the incident angle of the incident light, and includes a second light collection lens 131, an iris 132, and a photomultiplier tube (PMT) detector 133. The light that is directed to the sample and then scattered is collected by a collection lens 131, and some of the light is filtered by the iris 132 to reduce a light collection angle of the collected light as much as possible. The light passing through the iris 132 is transmitted to the PMT detector 133. The PMT detector 133 is connected with an autocorrelator board (e.g., Brookhaven Instruments Corporation, BI-9000AT) included in the computer 150.

In Exemplary Embodiment 1 as described above, optical adjustment is very easily conducted by the 180° detection geometry in which focusing of the incident light and collection of the Raman scattered light are performed by one objective lens 123. Also, independently from the Raman scattering detection means having a 180° detection geometry, the present embodiment shows an elastic scattering detection means with 90° geometry and thus it is easy to construct optical configuration and it has all the advantages of both the Raman scattering detection apparatus and the dynamic light scattering detection apparatus.

Exemplary Embodiment 2

Raman Scattering Detection in 90° Geometry and Light Scattering Detection in 90° Geometry This is a configuration in which scattered light collected in 90° light collection geometry is separated into Raman scattered light and elastic scattered light by notch and edge filters, thereby simultaneously detecting Raman scattering and light scattering. The 90° light collection geometry is a geometry which is the most commonly used in conventional Raman scattering and dynamic light scattering detection having advantages of the conventional optical configuration as it is. In the light scattering detection, a light condensing angle may be adjusted to small angle through the control of an iris if necessary.

Figure 2:
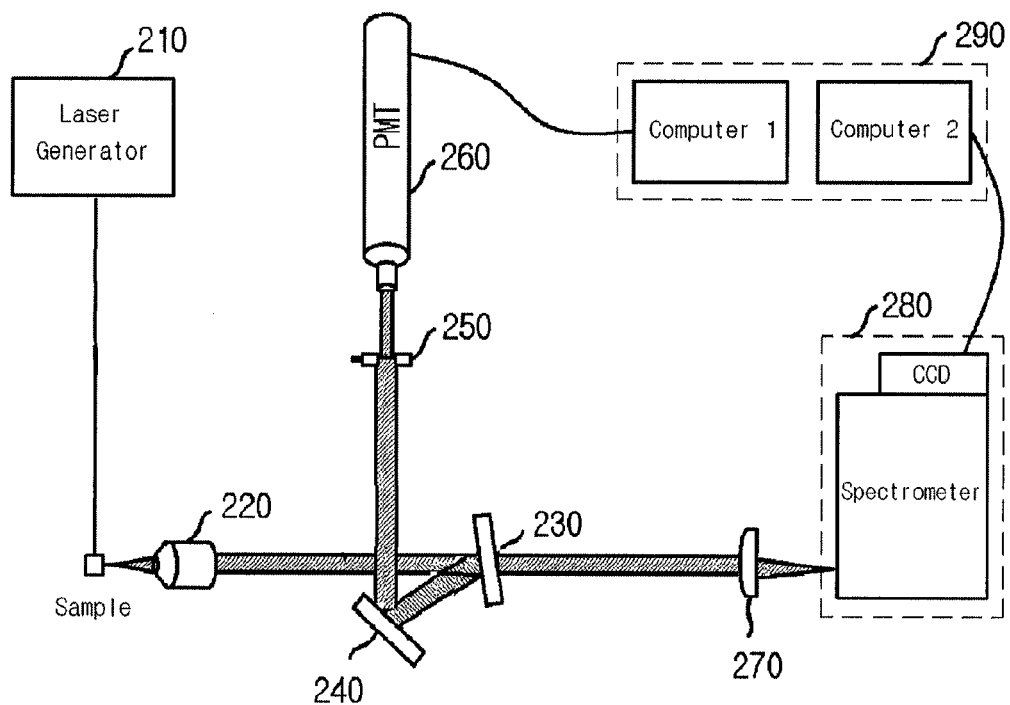
FIG. 2 illustrates a simultaneous detection apparatus of Raman scattering and dynamic light scattering according to another exemplary embodiment of the present invention.

FIG. 2 illustrates a simultaneous detection apparatus of Raman scattering and dynamic light scattering according to Exemplary Embodiment 2 of the present invention.

Referring to FIG. 2, it may be noted that the simultaneous detection apparatus of the Raman scattering and light scattering according to the embodiment has a Raman scattering detection means and a light scattering detection means, both having a 90° detection geometry. The geometry according to the present embodiment may have lower collection efficiency of Raman scattered light than that in Exemplary Embodiment 1, because a region in which incident light is condensed by a condenser lens is perpendicular to that in which signals are collected by an objective lens 220. However, the apparatus has relatively less noise caused by scattering and reflection of optical components formed along a progressive direction of the incident light. The dynamic light scattering detection can perform conventional right-angle geometry detection, and also determine a scattered light collection angle by control of an iris 250 included in the front of a PMT detector 260.

In the embodiment illustrated in FIG. 2, a laser beam generated from a laser generator 210 is directed to a sample through a condenser lens 211, and then collected by an objective lens 220. Among the collected light, only Raman scattered light is passed through a notch filter 230 and transmitted to a spectrometer 280, and the other scattered light is reflected to a mirror 240. The light reflected from the mirror 240 is transmitted to the PMT detector 260 via the iris 250. In FIG. 2, except the transmission step of the light, operations and functions of the PMT detector 260, a light collection lens 270, the spectrometer 280 and a computer 290 are the same as those in the embodiment illustrated in FIG. 1, and thus detailed descriptions thereof will be omitted.

Exemplary Embodiment 3

Raman Scattering Detection in 180° Geometry and Light Scattering Detection in 180° Geometry This is a configuration of separating scattered light condensed in 180° geometry into Raman scattered light and elastic scattered light using a notch filter and simultaneously detecting Raman scattering and light scattering. In order to embody the 180° light condensing geometry, a beam splitter is needed. In light scattering detection, a light condensing angle can be adjusted to small angle through control of an iris if necessary. Since the scattered light in 180° direction has a relatively smaller variation of an autocorrelation function with respect to a light condensing angle, a relatively larger light condensing angle may be used, but scattering intensity in this direction is also relatively small.

Figure 3:
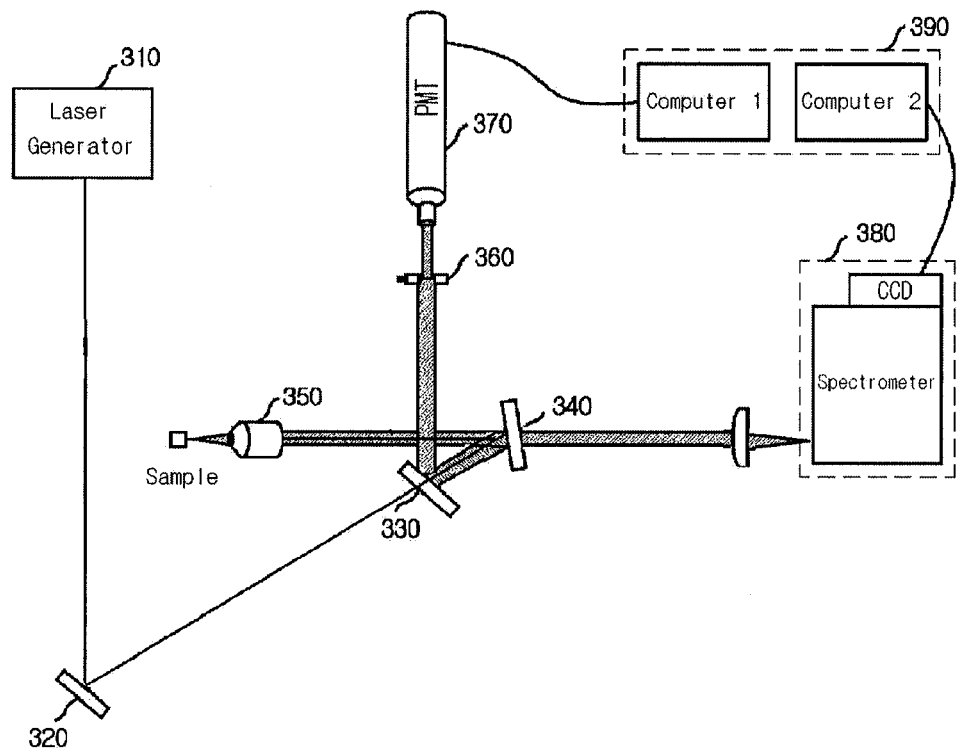
FIG. 3 illustrates a simultaneous detection apparatus of Raman scattering and dynamic light scattering according to still another exemplary embodiment of the present invention.

FIG. 3 illustrates a simultaneous detection apparatus of Raman scattering and light scattering according to Exemplary Embodiment 3 of the present invention.

Referring to FIG. 3, from this embodiment, it may be noted that the detection apparatus of Raman scattering and dynamic light scattering is placed at 180° with respect to incident light. In this embodiment, Raman scattered light and elastic scattered light are separated by a notch or edge filter 340, and the elastic light is transmitted to a PMT detector 370 by a beam splitter 330.

In the embodiment of FIG. 3, a laser beam generated from a laser generator 310 is reflected by a mirror 320, and then transmitted to the beam splitter 330. The beam splitter 330 transmits the scattered light to the PMT detector 370, which has incidence and reflection characteristics in an appropriate ratio (e.g., 50:50). Thus, the light passing through the beam splitter 330 is reflected on the filter 340 and directed to a sample by an objective lens 350. The light scattered from the sample is collected by the objective lens 350 and transmitted to the notch filter 340, and the notch filter 340 admits only the Raman scattered light and transmit it to a spectrometer 380. The scattered light reflected from the notch filter 340 is transmitted again to the PMT detector 370 by way of the beam splitter 330 and an iris 360. According to such a configuration, while a light collection angle of the objective lens increases, effective light collection angle for detecting the scattered light may be controlled by hole adjustment of the iris 360 included at the front of the PMT detector 370. In FIG. 3, except for the step of transmitting light, operations and functions of the PMT detector 370, the spectrometer 380 and the computer 390 are the same as those in the embodiment illustrated in FIG. 1, and thus detailed descriptions thereof will be omitted.

In this embodiment, as in FIG. 1, in collection and incidence of the scattered light, the focus is adjusted by the same objective lens, and thus it is very effective in collection of the scattered light. Also, since an optical configuration for simultaneous detection of Raman scattering and light scattering is very simple and performs 180° geometry light condensing using an objective lens, light condensing efficiency is very high. Such light condensing efficiency may sufficiently overcome light loss caused by a beam splitter having incidence and reflection characteristics at a specific ratio in FIG. 3.

In the above described embodiments, means used in detection of Raman scattering (e.g., a filter and a spectrometer) may be used in detection of an optical spectrum, for example, of fluorescence and phosphorescence as it is. Thus, simultaneous detection of light scattering and fluorescence as well as simultaneous detection of light scattering and Raman scattering is possible. Accordingly, changes in size of nanoparticles and changes of optical characteristics of them according thereto may be simultaneously detected. For example, in the course of formation of cadmium selenide (CdSe) quantum dots, size of the quantum dots and emission characteristics according thereto can be simultaneous detected.

<Detection Results of Changes in Intensity of Surface-Enhanced Raman Scattering According to the Degree of Coagulation Between Silver Nano Particles>

Surface-enhanced Raman scattering (hereinafter, referred to as SERS) in which Raman scattering averagely increases more than $10^6$ times on a surface of a specific metal nano structure has been well known for approximately 30 years. In the present invention, investigations which are related to variations in size and SERS intensity by coagulation between the nanoparticles are performed by using silver nanoparticles in solution which is difficult to be controlled and observed in general.

Figure 4:
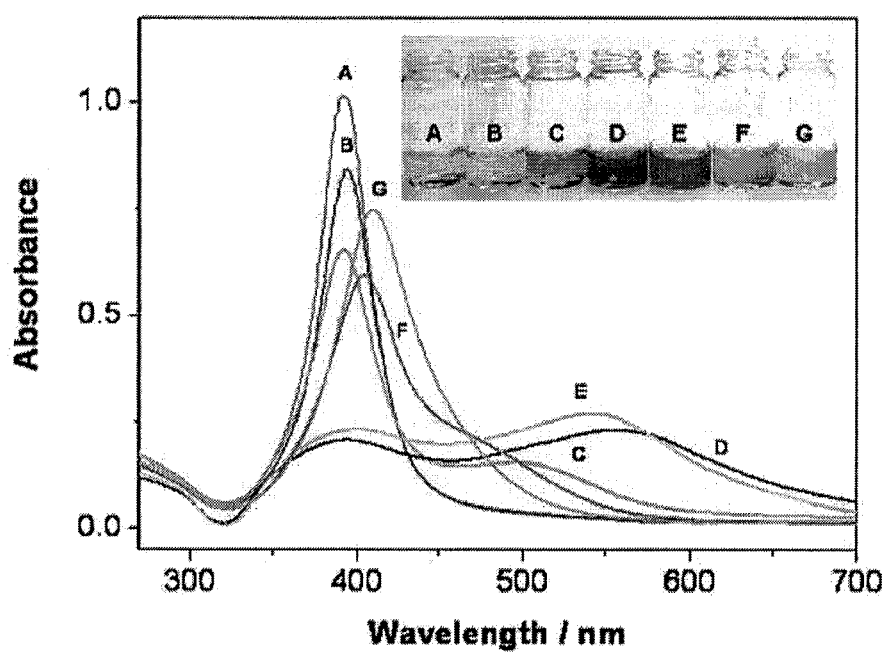
FIG. 4 illustrates a change of surface plasmon absorption observed when coagulation of silver nanoparticles is changed according to poly(4-vinyl pyridine (P4VP; MW60000, Aldrich) concentrations by treating the silver nano particles in aqueous solution with P4VP.

FIG. 4 illustrates variations of surface plasmon absorption observed due to the changes in coagulation between silver nanoparticles according to concentration of poly(4-vinylpyridine) (P4VP; MW 60000, Aldrich) after treating the silver nanoparticles in aqueous solution with poly(4-vinylpyridine). In FIGS. 4, A, B, C, D, E, F and G correspond to P4VP concentrations of 0, $5 \times 10^{-6}$, $1 \times 10^{-5}$, $5 \times 10^{-5}$, $1 \times 10^{-4}$, $5 \times 10^{-4}$ and $1 \times 10^{-3}$ g/dL, respectively. As a characteristic change, it is observed that from A to D, a novel adsorption band by the coagulation between silver nanoparticles is formed at a longer wavelength than 390 nm, and gradually leads to a red shift. However, from D to G, it is observed that this novel band leads to a blue shift, and is eventually put together with a band occurring around 390 nm. Such a change shows that interaction between the silver nanoparticles decreases as the concentration of P4VP increases more than a predetermined level, which means that a distance between the silver nano particles becomes greater as the P4VP concentration increases.

Figure 5:
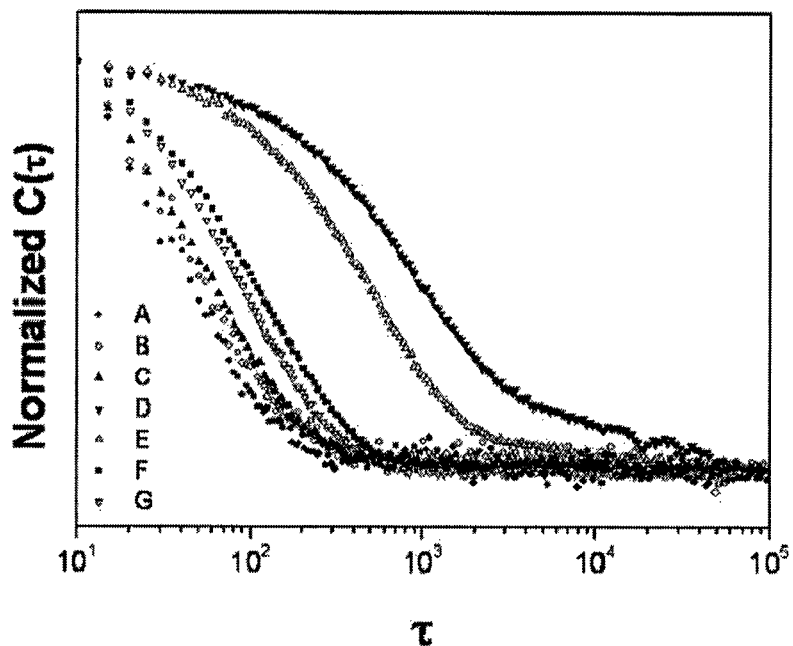
FIGS. 5 to 8 illustrate simultaneous detection results of dynamic light scattering and Raman scattering in order to observe changes in coagulation between silver nano particles due to P4VP and in size thereof, and SERS changes according thereto.
Figure 6:
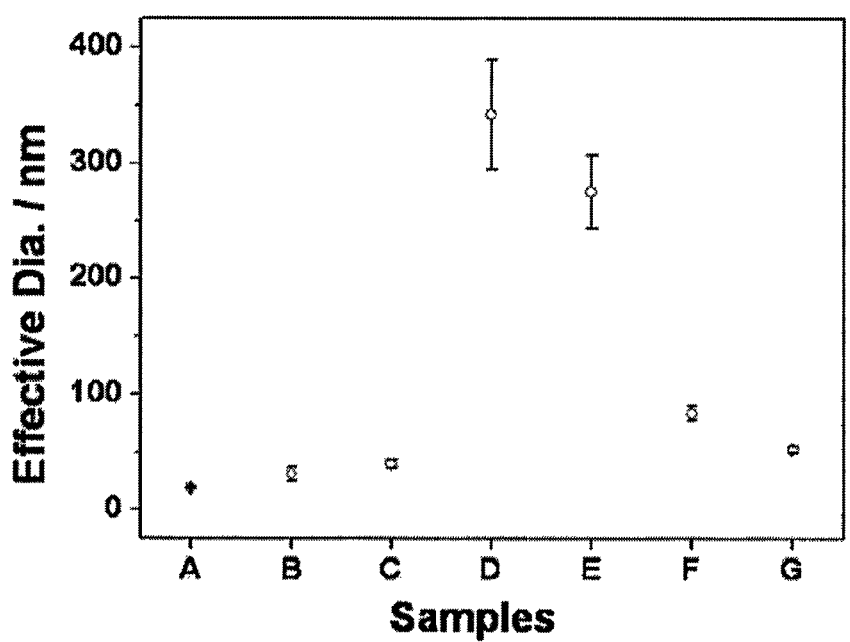

FIGS. 5 to 8 illustrate results of the simultaneous detection of dynamic light scattering and Raman scattering for observing SERS changes according to the degree of coagulation between silver nanoparticles and changes in size thereof due to P4VP. FIG. 5 illustrates temporal correlation profiles obtained from detected scattered light, and FIG. 6 illustrates distribution of nanoparticles obtained by analyzing the profiles. As illustrated in these drawings, it can be seen that the size of a nano particle is dramatically increased by the increase in concentration of P4VP and then decreased with the concentration change from D to G. This change corresponds to an observed tendency. Particularly, it can be seen that, from C to D, the size is drastically increased. This is because P4VP are absorbed to the surface of the silver nanoparticles to neutralize charge of the surface, and thus the silver nanoparticles are unstable and the coagulation therebetween is induced.

Figure 7:
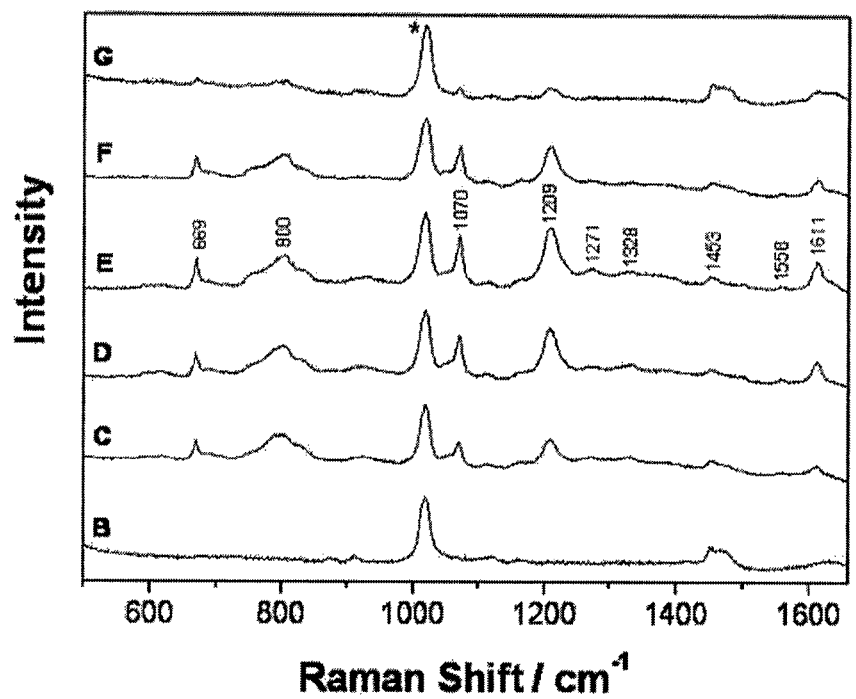
Figure 8:
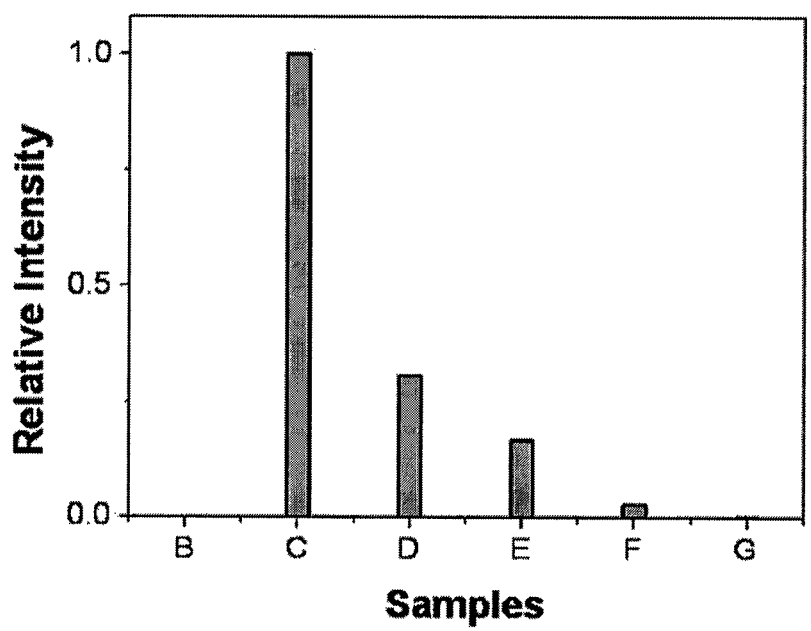

FIG. 7 illustrates a SERS spectrum of P4VP adsorbed to a surface of silver, which is simultaneously detected together with light scattering, and FIG. 8 illustrates intensity of a SERS signal standardized by dividing a 1019 $cm^{-1}$ Raman band into bands formed by solvents and concentrations of P4VP. In FIG. 8, as with the result of light scattering, the intensity of the SERS signal is increased and then decreased, which means that the intensity of the SERS signal does not become higher as the silver nanoparticles are further agglomerated, but it is to required that such an appropriate degree of coagulation to obtain higher intensity of the SERS signal. In C, the observed size is approximately 40 nm, which corresponds to approximately 10 nano particles on the assumption of a structure in which the silver nano particles are closely packed.

While the invention has been shown and described with reference to certain exemplary embodiments thereof, it will be understood by those skilled in the art that various changes in form and details may be made therein without departing from the spirit and scope of the invention as defined by the appended claims. For example, while dynamic light scattering has been mainly described with reference to exemplary embodiments of the present invention, it will be understood by those skilled in the art that the present invention may be applied to detection of static light scattering which is detected at various angles and does not use an autocorrelation function.

Thus, it may be understood that the scope of the present invention includes such changes, modifications or adjustments as well as the accompanying claims.

The invention claimed is:

1. An apparatus for simultaneous detection of Raman scattering and light scattering, comprising:
   a detection means for applying incident light to a sample at an angle of incidence, and detecting Raman scattering at 180° to the angle of incidence and light scattering at 90° to the angle of incidence to simultaneously collect the Raman scattering and the light scattering; and
   a computer connected to the detection means to obtain at least one of the size and distribution of particles in the sample from the detected light scattering, and to obtain information on a molecular structure of the sample from the detected Raman scattering.

2. The apparatus according to claim 1, wherein the detection means comprises:
   an objective lens for condensing the incident light on the sample and collecting scattered light from the sample;
   a filter for transmitting the incident light to the objective lens and allowing only the Raman scattered light of the light collected by the objective lens to selectively pass through;
   a spectrometer for analyzing a spectrum of the Raman scattered light passing through the filter;
   a light collection lens disposed perpendicular to the objective lens and collecting the scattered light from the sample;
   an iris for adjusting a light collection angle of the scattered light which is collected by the light collection lens; and
   a photomultiplier tube detector for receiving the scattered light passing through the iris.

3. An apparatus for simultaneous detection of Raman scattering and light scattering, comprising:
   a detection means for applying incident light to a sample at an angle of incidence, and detecting Raman scattering from the sample at 90° to the angle of incidence and light scattering from the sample at 90° to the angle of incidence; and
   a computer connected to the detection means to obtain at least one of a size and distribution of particles in the sample from the detected light scattering, and to obtain information of a molecular structure of the sample from the detected Raman scattering,
   wherein the detection means comprises:
   an objective lens disposed perpendicular to incident light and collecting scattered light from the sample;
   a filter for selectively allowing only the Raman scattered light of the light collected by the objective lens to selectively pass through, and reflecting elastically scattered light;
   a spectrometer for analyzing a spectrum of the Raman scattered light passing through the filter;
   an iris for adjusting a light collection angle of the elastically scattered light reflected by the filter; and
   a photomultiplier tube detector for receiving the elastic scattered light passing through the iris.

4. An apparatus for simultaneous detection of Raman scattering and light scattering, comprising:
   a detection means for applying incident light to a sample at an angle of incidence, and detecting Raman scattering at 180° to the angle of incidence and light scattering at 180° to the angle of incidence to simultaneously collect the Raman scattering and the light scattering; and
   a computer connected to the detection means to obtain at least one of the size and distribution of particles in the sample from the detected light scattering, and to obtain information on a molecular structure of the sample from the detected Raman scattering.

5. The apparatus according to claim 4, wherein the detection means comprises:
   an objective lens for condensing the incident light on the sample, and collecting the scattered light from the sample;
   a filter for transmitting the incident light to the objective lens, allowing only the Raman scattered light of the light collected by the objective lens to selectively pass through, and reflecting elastically scattered light;
   a beam splitter for transmitting the incident light to the filter, and reflecting at least a part of the elastically scattered light which is reflected by the filter;

an iris for adjusting a light collection angle of the elastically scattered light which is reflected by the beam splitter; and
a photomultiplier tube detector for receiving the elastically scattered light passing through the iris.

6. The apparatus according to claim 5, wherein a position, a shape and a size of the iris are adjustable to control the light collection angle, and thus light scattering is capable of being detected at various angles.

7. An apparatus for simultaneous detection of light scattering and an optical spectrum of one of fluorescence and phosphorescence, comprising;
a detection means for applying incident light to a sample at an angle of incidence, and detecting one of fluorescence and phosphorescence at 180° to the angle of incidence and light scattering at 90° to the angle of incidence to simultaneously collect the light scattering and the optical spectrum of one of fluorescence and phosphorescence; and
a computer connected to the detection means to obtain at least one of the size and distribution of particles in the sample from the detected light scattering, and to obtain information on a molecular structure of the sample from the detected optical spectrum of one of fluorescence and phosphorescence.

8. The apparatus according to claim 7, wherein the detection means comprises:
an objective lens for condensing the incident light on the sample and collecting scattered light from the sample;
a filter for transmitting the incident light to the objective lens and allowing only one of fluorescence and phosphorescence of the light collected by the objective lens to selectively pass through;
a spectrometer for analyzing the detected optical spectrum of one of fluorescence and phosphorescence of the light passing through the filter;
a light collection lens disposed perpendicular to the objective lens and collecting the scattered light from the sample;
an iris for adjusting a light collection angle of the scattered light which is collected by the light collection lens; and
a photomultiplier tube detector for receiving the scattered light passing through the iris.

9. An apparatus for simultaneous detection of light scattering and an optical spectrum of one of fluorescence and phosphorescence; comprising:
a detection means for applying incident light to a sample at an angle of incidence, and detecting one of fluorescence and phosphorescence from the sample at 90° to the angle of incidence and light scattering from the sample at 90° to the angle of incidence; and
a computer connected to the detection means to obtain at least one of a size and distribution of particles in the sample from the detected light scattering, and to obtain information of a molecular structure of the sample from the detected optical spectrum of one of the fluorescence and the phosphorescence,
wherein the detection means comprises:
an objective lens disposed perpendicular to incident light and collecting scattered light from the sample;
a filter for selectively allowing only one of fluorescence and phosphorescence of the light collected by the objective lens to selectively pass through, and reflecting elastically scattered light;
a spectrometer for analyzing the optical spectrum of one of fluorescence and phosphorescence passing through the filter;
an iris for adjusting a light collection angle of the elastically scattered light reflected by the filter; and
a photomultiplier tube detector for receiving the elastic scattered light passing through the iris.

10. An apparatus for simultaneous detection of light scattering and an optical spectrum of one of fluorescence and phosphorescence; comprising:
a detection means for applying incident light to a sample at an angle of incidence, and detecting one of florescence and phosphorescence at 180° to the angle of incidence and light scattering at 180° to the angle of incidence to simultaneously collect the light scattering and the one of the florescence and the phosphorescence; and
a computer connected to the detection means to obtain at least one of the size and distribution of particles in the sample from the detected light scattering, and to obtain information on a molecular structure of the sample from the detected optical spectrum of one of florescence and phosphorescence.

11. The apparatus according to claim 10, wherein the detection means comprises;
an objective lens for condensing the incident light on the sample, and collecting the scattered light from the sample;
a filter for transmitting the incident light to the objective lens, allowing only one of florescence and phosphorescence of the light collected by the objective lens to selectively pass through, and reflecting elastically scattered light;
a beam splitter for transmitting the incident light to the filter, and reflecting at least a part of the elastically scattered light which is reflected by the filter;
an iris for adjusting a light collection angle of the elastically scattered light which is reflected by the beam splitter; and
a photomultiplier tube detector for receiving the elastically scattered light passing through the iris.

12. The apparatus according to claim 11, wherein a position, a shape and a size of the iris are adjustable to control the light collection angle, and thus light scattering is capable of being detected at various angles.

* * * * *